United States Patent [19]

Chantler et al.

[11] Patent Number: 5,013,544
[45] Date of Patent: May 7, 1991

[54] CONTRACEPTIVE METHODS AND COMPOSITIONS

[75] Inventors: Eric N. Chantler, Marple Bridge; Max Elstein, Didsbury, both of England

[73] Assignee: The Victoria University of Manchester, Manchester, England

[21] Appl. No.: 471,699

[22] Filed: Jan. 29, 1990

Related U.S. Application Data

[63] Continuation of Ser. No. 238,667, Aug. 31, 1988, abandoned.

[30] Foreign Application Priority Data

Jun. 1, 1988 [GB] United Kingdom ............... 8812928

[51] Int. Cl.$^5$ .................... A61K 31/74; A61K 31/155
[52] U.S. Cl. ............... 424/78; 424/DIG. 14; 514/635; 514/841; 514/843
[58] Field of Search ............ 424/78, DIG. 14; 514/841, 843, 635

[56] References Cited

U.S. PATENT DOCUMENTS

| | | | |
|---|---|---|---|
| 4,590,070 | 5/1986 | Chantler et al. | 514/635 |
| 4,602,042 | 7/1986 | Chantler et al. | 514/843 |
| 4,795,761 | 1/1989 | Curtis-Prior | 514/613 |

FOREIGN PATENT DOCUMENTS 0247251 12/1987 European Pat. Off. .

OTHER PUBLICATIONS

CA 104:162116k, "Comparison of Action of Nonoxynol-9 and Chlorhexidine on Sperm", Sharman et al. (1986).

CA 103: 206801r, "A Comparison of Effects of Nonoxynol-9 and Chlorhexidine on Sperm Motility", Louis et al. (1985).

*Primary Examiner*—Lester L. Lee
*Assistant Examiner*—Carmen Pili-Curtis
*Attorney, Agent, or Firm*—Cushman, Darby and Cushman

[57] ABSTRACT

Pharmaceutical compositions comprising a combination of a polymeric biguanide and a spermicidal surfactant, useful for contraceptive purposes, for their spermicidal or sperm-immobilizing effect, and contraceptive methods and devices using them.

The polymeric biguanide is preferably a compound as described in U.K. Patent Specification No. 702,268 or a bisbiguanide as described in U.K. Patent Specification No. 705,838 or 1,095,902, but especially chlorhexidine. The spermicidal surfactant may be derived from ethylene oxide, preferably a condensate of nonylphenol and ethylene oxide, and especially with 9 to 11 molecular proportions thereof.

To avoid short-lived activity, the compositions are preferably made substantially free from anions (notably halide ions and especially chloride ions) which cause deactivation, apparently by reducing the solubility of the active ingredients.

7 Claims, No Drawings

CONTRACEPTIVE METHODS AND COMPOSITIONS

This is a continuation of application Ser. No. 07/238,667 filed Aug. 31, 1988 which was abandoned upon the filing hereof.

This invention relates to contraceptive methods, and in particular it relates to improved methods which utilise combinations of known spermicidal or sperm-immobilising agents, a spermicidal or sperm-immobilising method, and improved pharmaceutical compositions useful in such methods.

It is known that a number of compounds which are ethylene oxide condensates derived from phenolic compounds not only have detergent or surfactant properties but also are active as spermicides and are widely used as a spermicidal component in contraceptive and spermicidal preparations. A particular example of such a spermicidal surfactant compound is that known as nonoxynol-9. (U.S. Pat. No. 3,541,103; S. V Sender, Ortho Pharmaceuticals.)

It is also known that polymeric biguanide compounds have properties which make them useful) for contraceptive purposes. The term "polymeric biguanide" is used here to include the bisbiguanides as well as the higher polymeric biguanides containing more than two biguanide moieties. (European Patent Application No. 8430945.3, Publication No. 0138304, and European Patent Application No. 8430946.1, Publication No. 0138305, of Imperial Chemical Industries PLC).

A particular example of such a spermicidal polymeric biguanide compound is that known as chlorhexidine, which is also commonly used for its antiseptic properties.

We have now found that these two groups of compounds show a very marked and unexpected synergistic action when used in combination with each other in spermicidal or sperm-immobilising compositions.

Thus according to the present invention there are provided new pharmaceutical compositions, useful as spermicidal or sperm-immobilising compositions, as comprising both a polymeric biguanide and a spermicidal surfactant as active ingredients.

According to a further feature of the invention there is provided a contraceptive method which comprises applying to the vagina of a female mammal a spermicidal or sperm-immobilising amount of a combination of (a) a polymeric biguanide and (b) a spermicidal surfactant.

According to the invention there are also provided improved pharmaceutical compositions, useful for spermicidal or sperm-immobilising purposes, comprising a combination of (a) a polymeric biguanide and (b) a spermicidal surfactant.

The term "polymeric biguanide" is used here to include the bis-biguanides as well as the higher polymeric biguanides containing more than two biguanide moieties.

Both the components are well known in the art. For example the polymeric biguanides are referred to in detail not only in the European Patent Specifications identified above, but are fully described in United Kingdom Patent Specification Nos. 705,838 and 1,095,902 (which describe bis-biguanides) and No. 702,268 (which describes polymeric biguanides), where they are stated to possess good anti-bacterial and/or antifungal activity.

One group, more fully described in BP No. 702,268, comprises polymeric biguanide compounds which in their free base form are linear polymers in which the recurring unit is represented by the formula:

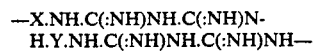

wherein X and Y stand for bridging groups in which together the total number of carbon atoms directly interposed between the adjacent nitrogen atoms is greater than 9 and less than 17. They may be in their free base form or as acid-addition salts thereof. The acid component of such salts should be a pharmaceutically acceptable acid, for example hydrochloric acid, acetic acid, gluconic acid, or mixtures thereof.

The said bridging groups may consist of polymethylene chains, which optionally may be interrupted, for example by oxygen and/or sulphur atoms, and also may incorporate cyclic nuclei which themselves may be saturated or unsaturated. The number of carbon atoms directly interposed between the nitrogen atoms when the group X and/or Y incorporate a cyclic group or groups includes those in which that segment of the cyclic group or groups which is the shortest.

A preferred polymeric biguanide for the purposes of this invention is that in which X represents $-(CH_2)_2-$ to $-(CH_2)_{12}-$ and preferably $-(CH_2)_6-$, Y represents $-(CH_2)_2-$ to $-(CH_2)_{12}-$ and preferably $-(CH_2)_6-$, and which has a number average molecular weight of about 500 to 20,000, and especially preferred is a mixture of polymeric biguanides represented by the formula:

wherein n varies from about 5 to 10, and having a number average molecular weight of about 100 to 2200, for example in the form of their salts with hydrochloric acid.

Another group, more fully described in BP Nos. 705,838 and 1,095,902, comprises bis-biguanide compounds of the formula:

$$R^1R^2N.C(:NH)N:C(NH_2)N-A-N.C(NH_2):N.C(:NH)NR^3R^4 \qquad (I)$$

wherein either (i) $R^1$ and $R^3$, which may be the same or different, are each a phenyl radical which is substituted by alkyl, alkoxy, nitro or halogen, $R^2$ and $R^4$ are both hydrogen, and A is a 3–9C polymethylene diradical, wherein the polymethylene chain may be interrupted by oxygen atoms and/or by aromatic nuclei; or (ii) the bivalent bridge A is:
  (a) alkylene from 2 to 12 carbon atoms having the valence bonds attached to different carbon atoms,
  (b) $-(CH_2)_m-X-(CH_2)_n-$ wherein m and n each represent an integer from 2 to 6 and X is O or S, (c)

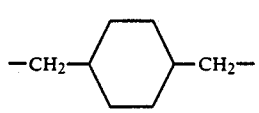

-continued

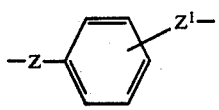

wherein Z and Z¹ are each alkylene of from 1 to 3 carbon atoms,

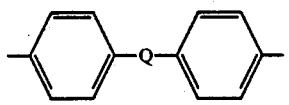

wherein Q is —O—, —S—, —SO— or —SO$_2$—,

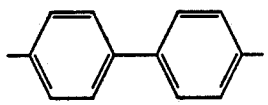

or

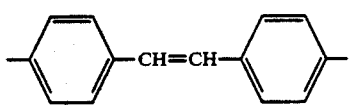

R¹ and R³ are each:
(a) alkyl of from 6 to 16 carbon atoms, or
(b) alkyl-Y-alkylene, wherein Y is O or S and the alkyl and alkylene radicals together contain 3 to 15 carbon atoms;

For example the preferred polymeric biguanide is available commercially under the name chlorhexidine, and has the chemical name 1:6-di-(N-p-chlorophenyl-diguanido)-hexane. [Formula (I) above, with R¹=R³=p-chlorophenyl, R²=R⁴=hydrogen, and A=—(CH$_2$)$_6$—]. Another is the compound of formula (I) above, with R¹=R³=2-ethyl-hexyl, R²=R⁴=hydrogen, and A=—(CH$_2$)$_6$—]. These may be in a salt form, derived from a pharmaceutically acceptable acid, for example the diacetates, digluconates, dihydrochlorides or mixtures thereof.

The spermicidal surfactants useful for the purposes of this invention include any of the non-ionic surface active agents which have spermicidal activity, and especially the condensates of nonylphenol with polyethylene oxide. For example, the condensate known and available in commerce under the name nonoxynol-9 and represented by the formula:

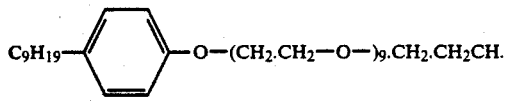

is especially well known and used as a spermicidal component in contraceptive preparations. Such a product is not necessarily a single pure compound of this formula but a mixture of condensates containing different proportions of ethylene oxide but having the overall statistically averaged composition indicated. Another example is the product commonly known as nonoxynol-11, which is represented by the formula:

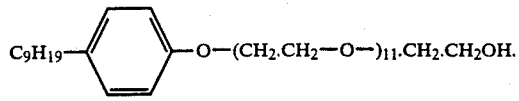

The amounts of the two components may be any which are adequate to produce a spermicidal or sperm-immobilising effect.

The proportions of the two components relative to each other may vary, and are preferably in the range 10:1 to 1:10 (of the polymeric biguanide to the surfactant, calculated by weight) but other proportions outside this range may be used if desired.

In vitro, the combination of active compounds exert their spermicidal or sperm-immobilising effect over a range of concentrations, the minimum being approximately 0.15% (calculated as weight/volume) in contact with an equal volume of semen. The preferred concentration for use in vivo should be at least 10 times this at any location at which the effect is required.

It has been found that the polymeric biguanide component, and especially chlorhexidine, has a marked tendency to lose its spermicidal activity in some circumstances and formulations. The mechanism for this loss of activity is not fully understood, but it is sufficiently rapid to result in a loss of storage life if the effect is not recognised.

The effect is associated with certain anions, which have this deactivating effect. The undesired anions are principally inorganic ions, and include especially the halide anions (for example chloride ions) and multi-charged anions (for example phosphate ions). These are referred to here conveniently as "undesired anions."

Even at low concentrations, the effect can be rapid. For example, chloride ion at physiological concentrations (i.e. the levels present in physiological media and fluids) can cause chlorhexidine to lose its spermicidal activity in less than two hours. By comparison, an aqueous solution of chlorhexidine acetate prepared in isotonic aqueous sucrose solution remained stable for greater than three days.

The mechanism is not clear but is believed to be in some way associated with some degree of crystallisation or loss of solubility, though not to the level of positive visible precipitation from solution. It is considered that the effect is due to some incipient crystallite formation, which leads to a progressively increasing loss of bio-available chlorhexidine.

Accordingly we prefer, in the methods and compositions of the invention, to use the active agents (the polymeric biguanide and the non-ionic surfactant) in the substantial absence of such anions. This is particularly important for compositions which are desired to have an effective active life greater than an hour or so, for example a storage life for a product which is intended to be kept for a time before use or which cannot readily be freshly made up immediately before use.

If total exclusion of such undesired anions is not practicable, then at least it is preferred to keep the concentration of such anions as low as is practicable, for example by ensuring that water and other components from which compositions are made are chosen so at to avoid including these anions. For example, this can be done by using components containing only those anions which are normal counter-ions for the polymeric biguanide (for example chlorhexidine) and do not fall into the category of undesired anions as discussed above, for example by using chlorhexidine as an organic salt (for example the acetate or the gluconate) or as a non-salt form.

If it desired to make the compositions of the invention isotonic with body fluids, then this should be done with additive which are sustantially free from the undesired anions. Likewise, if it is desired to modify the physical properties of the compositions, for example to make gels, then it is preferred to use additives substantially free from the undesired anions.

For use, the pharmaceutical compositions may be formulated to contain convenient levels of active ingredients to produce such effective levels at the location in vivo. This is preferably in the range 0.5% to 10%, and usually at least 3%, of the pharmaceutical composition, on a weight/volume basis. The most suitable concentration in any particular case will be determined to some degree by the particular mode and quantities of the composition intended for practical use.

The compositions of the invention may be formulated in any form any which is suitable or convenient for use and may contain any of the adjuvants or excipients conventional for such compositions and appropriately compatible with the active ingredients and each other. For example they may be in the form of a pessary, cream, liquid douche, gel, aerosol foam, or impregnated tampon, or in a controlled delivery device of the compounds in a polymer matrix. They may be used in the ways already known, for example by application to the vagina in a conventional manner.

The advantages of the invention are that the desired level of spermicidal or sperm-immobilising action can be achieved by use of smaller amount or concentration of active chemical than by use of either component alone, and such reductions in usage of chemicals is often regarded as a desirable objective.

The inclusion of chlorhexidine has advantages as it acts as a spermicide both in the vagina and in the cervical mucus. This is in contrast to nonoxynol-9, which is only spermicidal in the vagina and does not enter the cervical mucus.

The invention is illustrated but not limited by the following Examples in which the parts and percentages are by weight unless otherwise stated.

EXAMPLE 1

Test Method

Chlorhexidine, as the diacetate salt, and/or nonoxynol-9 (50 μl. of an appropriate aqueous dilution) was dissolved in Tyrodes T6 balanced salt solution supplemented with 4 mg./ml. of human albumin. The solution was prepared and used immediately, by being mixed with 50 μl. of fresh human semen with a sperm concentration of at least 50 million per ml, and a motility of at least 80%, and incubated at 25 degrees C. for about 1 minute.

The motility of the sperm so treated was measured by one of two methods:

(1) If the concentration of chlorhexidine caused protein precipitation, motility was estimated by phase contrast microscopy at 200× magnification in a 10 μm deep counting chamber.

(2) If the solution remained optically clear, motility was measured by laser Doppler spectroscopy. This technique involves the analysis by auto-correlation of the fraction of the scattered laser light which contains the Doppler-shifted frequencies generated by interaction between the incident laser and the sperm head.

Test Results

The results are summarised in the following Table:

| | Active ingredient and concentration. | | % Inhibition of motility. |
|---|---|---|---|
| A. | Chlorhexidine | 2 mg./ml. | 5 |
| B. | Chlorhexidine | 0.5 mg./ml. | ZERO |
| C. | Nonoxynol-9 | 2 mg./ml. | 100 |
| D. | Nonoxynol-9 | 0.5 mg./ml. | ZERO |
| E. | Chlorhexidine and Nonoxynol-9 | 2 mg./ml. 0.5 mg./ml. | 100 |

These results were derived from the analysis of the effects of the compounds on three ejaculates from different men, each analysed in duplicate over the range 0 to 2 mg./ml. of each of the active ingredients.

They demonstrate clearly the synergistic effect of the two compounds in combination.

EXAMPLE 2

The procedure of Example 1 was repeated, using solutions of the specified compounds (nonoxenol-9 and chlorhexidine diacetate) in an isotonic aqueous solution of sucrose, the spermicidal action of nonoxenol-9 and chlorhexidine diacetate, derived from five examinations, each being measured in duplicate. The concentrations are the final values in semen.

The values expressed are the percentages, expressed as a mean, of the sperm which are motile 1 minute after contact with the spermicide.

The results are summarised in the following Table:

| | X | | | |
|---|---|---|---|---|
| Y | 0 | 0.2 | 0.4 | 0.6 |
| 0 | 50.37 | 31.09 | 0 | 0 |
| 0.5 | 39.32 | 7.34 | 0 | 0 |
| 1.0 | 16.14 | 2.20 | 0 | 0 |
| 2.0 | 10.02 | 0 | 0 | 0 |
| 5.0 | 0 | 0 | 0 | 0 |

(X) Nonoxynol-9 concentration (mg/ml.)
(Y) Chlorhexidine concentration (mg./ml.)

Similar results were obtained by using chlorhexidine digluconate in place of the diacetate.

The activity of the composition made up in isotonic sucrose was observed to remain stable for periods of greater than 3 days.

What is claimed is:

1. A pharmaceutical composition useful for spermicidal or sperm-immobilizing purposes consisting essentially of a combination of chlorhexidine and a spermicidal surfactant which is a nonylphenol/ethylene oxide condensate wherein the proportion of chlorhexidine to the surfactant is in the range of 10:1 to 1:10, by weight, said combination providing a synergistic spermicidal or sperm-immobilizing effect compared to use of the chlorhexidine or surfactant separately.

2. Pharmaceutical composition as claimed in claim 1, wherein the spermicidal surfactant is a condensate which contains 9 to 11 molecular proportions of ethylene oxide for each molecular proportion of nonylphenol.

3. Pharmaceutical composition as claimed in claim 1, wherein the spermicidal surfactant is nonoxynol-9 and-/or nonoxynol-11.

4. Pharmaceutical composition as claimed in claim 1, in a form substantially free from chloride ions and other ions which cause insolubilization of the polymeric biguanide.

5. Pharmaceutical composition as claimed in claim 1, wherein the proportion of the active ingredients is in the range 0.5% to 10%.

6. Pharmaceutical composition as claimed in claim 1, wherein the composition is isotonic with body fluids.

7. A contraceptive method which comprises applying to the vagina of a female mammal a spermicidal or sperm-immobilising amount of a composition as claimed in claim 1.

* * * * *